United States Patent [19]

Bellhouse

[11] Patent Number: 4,611,579

[45] Date of Patent: Sep. 16, 1986

[54] LARYNGOSCOPE

[75] Inventor: Christopher P. Bellhouse, Murwillumbah, Australia

[73] Assignee: Avulunga Pty Ltd., Murwillumbah, Australia

[21] Appl. No.: 602,760

[22] Filed: Apr. 23, 1984

Related U.S. Application Data

[63] Continuation of Ser. No. 318,198, Nov. 4, 1981, abandoned.

[30] Foreign Application Priority Data

Nov. 10, 1980 [AU] Australia ............................... PE6412
Nov. 11, 1980 [AU] Australia ............................... PE6436

[51] Int. Cl.⁴ .................................................. A61B 1/06
[52] U.S. Cl. ........................................................ 128/11
[58] Field of Search ...................... 128/10, 11, 200.26

[56] References Cited

U.S. PATENT DOCUMENTS

| | | | |
|---|---|---|---|
| 3,643,654 | 2/1972 | Felbarg | 128/11 |
| 4,114,609 | 9/1977 | Moses | 128/11 |
| 4,314,551 | 2/1982 | Kadell | 128/11 |
| 4,337,761 | 7/1982 | Upster | 128/11 |

Primary Examiner—Edward M. Coven
Assistant Examiner—Max F. Hindenburg
Attorney, Agent, or Firm—Cushman, Darby & Cushman

[57] ABSTRACT

This invention relates to a laryngoscope blade which includes a pair of opposed substantially straight portions so as to form a generally V shaped blade of relatively shallow included angle wherein the blade is substantially L shaped or Z shaped in cross section throughout at least part of its length whereby when said blade is inserted in the patients mouth substantially direct vision of the larynx may be obtained. Preferably the blade is substantially L shaped throughout the major part of it length.

The invention also relates to a prism for laryngoscope blade or laryngoscope having a leading end surface, a top surface and a trailing end surface in side view. The leading end surface may slope rearward at an acute angle to horizontal and thereafter emerge into a top surface which also slopes rearwardly, but at a shallower angle to horizontal before forming said trailing end surface. The end surface may slope downwardly from the top surface. The leading end surface may be relatively short in length compared to the top surface and the trailing end surface may be longer than the leading end surface.

6 Claims, 17 Drawing Figures

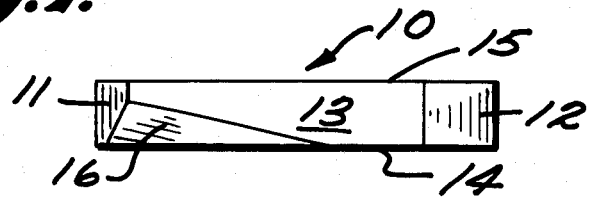
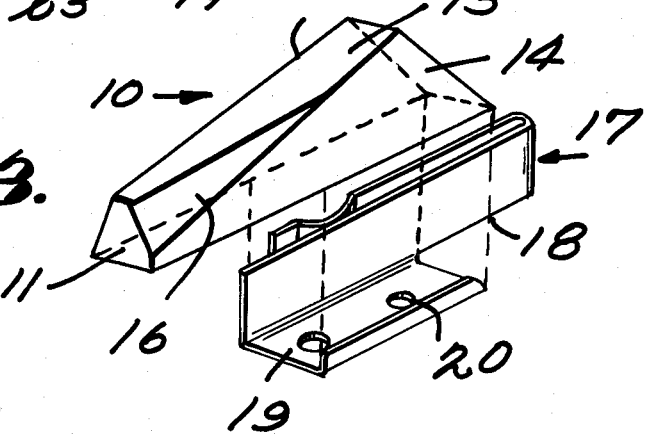
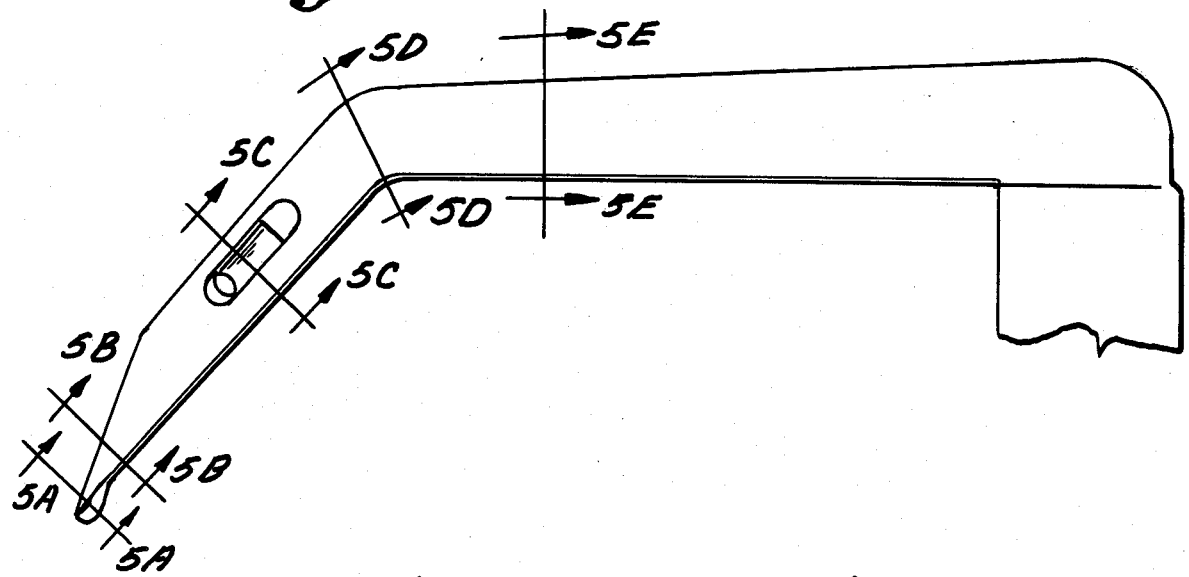

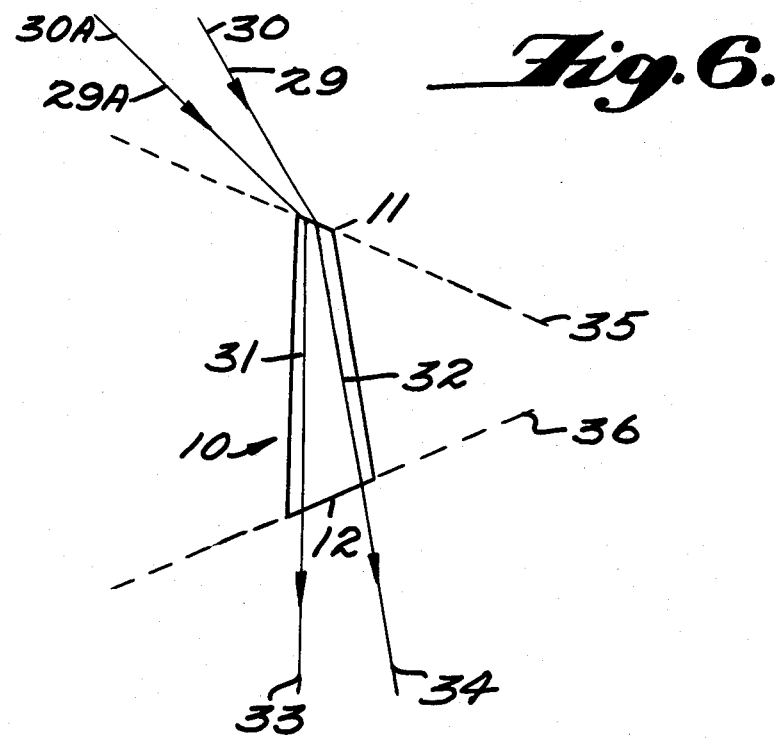
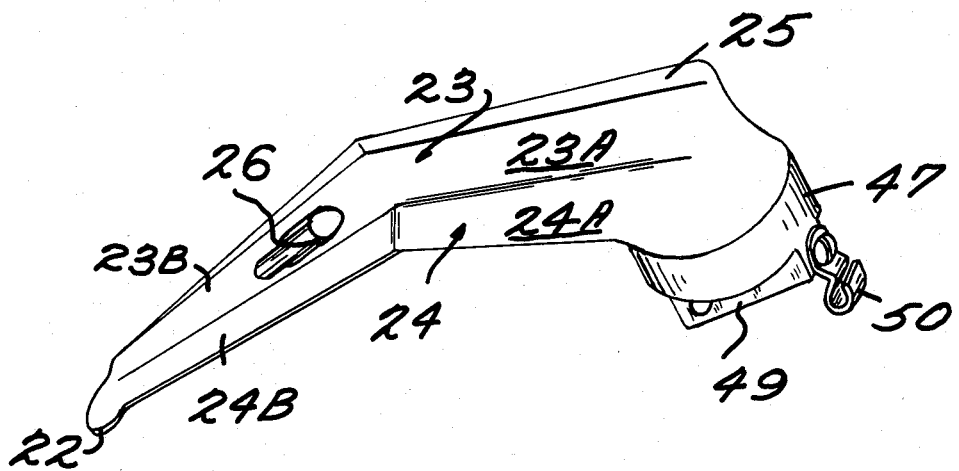

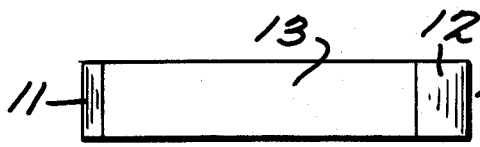
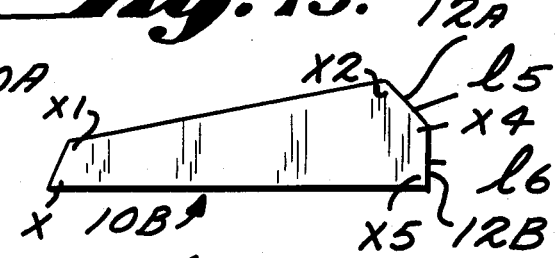
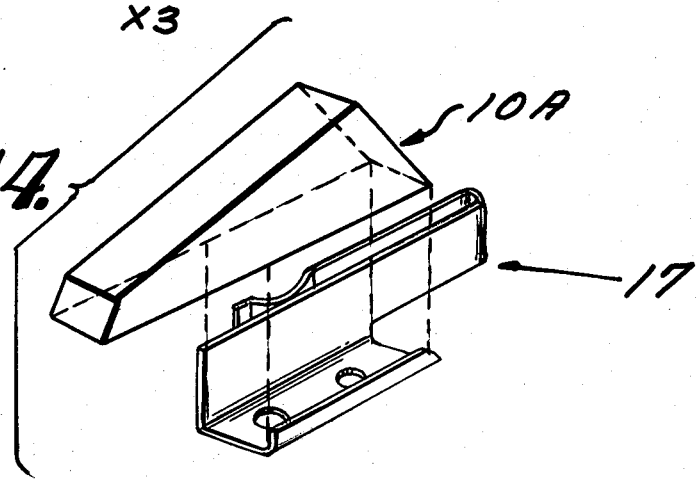
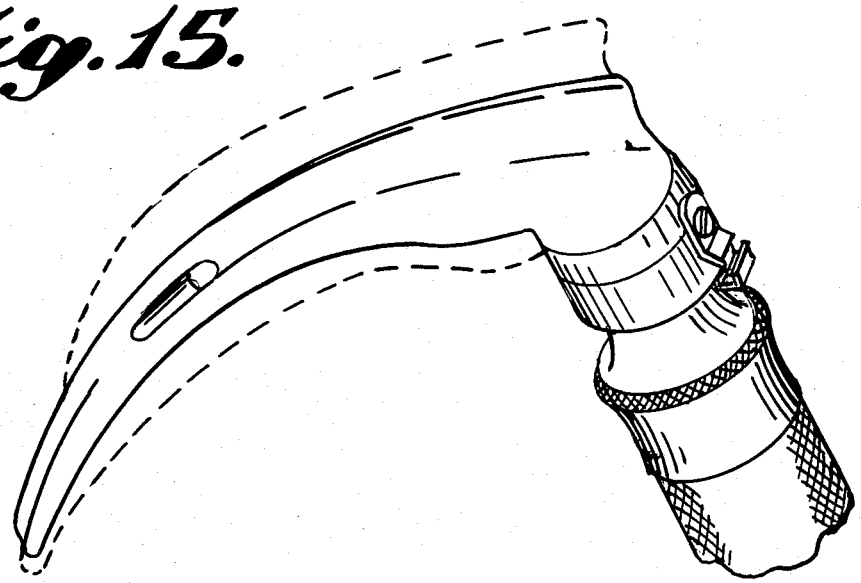

LARYNGOSCOPE

This is a continuation of application Ser. No. 318,198, filed Nov. 4, 1981, now abandoned.

This invention relates to an improved laryngoscope.

Laryngoscopes are instruments utilized in general anaesthesia and are used to expose the larynx to the vision of an anaesthetist whereby the larynx is illuminated by a lamp incorporated in the laryngoscope. Normally the laryngoscope is used to hold the tongue forward of the line of vision so that a clear vision of the larynx may be obtained. The anaesthetist can then introduce the distal end of a rubber tube (i.e. known as an endotracheal tube) into the larynx and connect the proximal end to anaesthetic apparatus. The rubber tube is used for general anaesthesia and is desirable if there is substantial quantities of blood or other fluid in a patient's throat or if access is to be provided for surgery of the head or neck or again if a particular operation requires that the patient's muscles be in a relaxed state. In the latter case the anaesthetist needs to be able to inflate the patient's lungs periodically.

With existing laryngoscopes difficulty is experienced in displaying the larynx and inserting the rubber tube if there is bony abnormality in the patient's neck or jaws or soft tissue abnormality at the mouth, or tongue or tissues in front of the neck. In these cases the anaesthetist will not be able to manipulate the patient's head sufficiently into a "sword swallowing" position and thus will generally not be able to hold the tongue forward from the line of vision to allow a view of the larynx.

Because this difficulty is a very serious handicap which occurs in about five per cent of adults, many attempts have been made to find a solution. In some cases surgical techniques such as tracheostomy (surgical opening of the trachea) and direct insertion of the endotracheal tube have been used. Alternatively another technique involved puncturing the neck, inserting a fine catheter through the larynx up to the mouth and subsequently "railroading" an endotracheal tube over the catheter down into the trachea.

In addition to the above there have been various modifications made to the conventional laryngoscope which have only met with limited success. These modifications include the use of a mirror or prism so as to provide an indirect method of viewing of the trachea. Conventional laryngoscope blades are normally of two types. One is a curved blade which is placed anteriorly to the epiglottis and exposing the larynx by pulling the blade straight anteriorly. Another is the straight blade which is inserted below the tip of the epiglottis which is then elevated by the tip of the blade thus exposing the larynx. However, although these conventional laryngoscope blades operate efficiently for normal adults, in the special five percent category referred to above, difficulty can be experienced.

Possibly the most widely used curved laryngoscope blade is that known as the Macintosh blade which includes a handle, a blade having a top horizontal flange which is attached to the top of a vertically extending web or vertical component, and a lower horizontal flange extending from the bottom of the web on the opposite side to that of the top flange. The Macintosh blade is relatively short when compared to a long straight laryngoscope blade and has a pronounced upward or concave curvature relative to the handle.

Although the Macintosh blade frequently does not allow display of the entire glottis, it generally provides sufficient exposure of the larynx to permit identification of landmarks and intubation of the trachea. Furthermore the curved shape distances its proximal end from the upper teeth, allowing intubation with little risk of damage. In practice it is generally of little importance that the tip of the endotracheal tube approaches the larynx at a substantial angle to the line of the trachea, rather than in the line of the trachea as happens when a Jackson or straight type of laryngoscope is used.

However, as mentioned above, in the special case referred to above where difficulty is experienced by the abovementioned anatomical abnormalities, the Macintosh laryngoscope blade falls down mainly on two main areas.

Firstly, to adequately expose the larynx, the blade must be pulled well forward so that the tip, lying in the vallecular fossa and obscured by the curve of the blade, is well forward of the larynx, leaving sufficient of the glottis visible behind the curve of the blade. When the blade cannot be pulled forward to this extent the hump or concave curvature of the blade obliterates direct vision of the larynx.

Secondly, where it is difficult to expose the larynx the anaesthetist must "go to the corner of the mouth" and insert the laryngoscope blade laterally to the upper incisor teeth, over the anterior pillar of the tonsil and in the sulcus between tongue and tonsil. In many patients the blade it too wide to do this adequately. The vertical component of the Macintosh blade normally holds the tongue to the left side of the mouth and along this vertical flange or component are usually located the electrical connections to the lamp. In a patient with a very small mouth or very prominent teeth, this component has been found to be too high to allow adequate insertion of the laryngoscope blade.

In 1968 Huffman, in order to overcome this problem introduced a prism to be attached to a Macintosh blade by a steel clip. In some cases the prism provided an indirect view of the larynx. However, it has normally not been necessary for straight forward endotracheal intubations and has been found to be too bulky to leave sufficient room in the mouth for an endotracheal tube where laryngoscopy is difficult such as in the special category already discussed above where patients have anatomical abnormality.

In 1956 Siker produced a laryngoscope blade which was angulated or V shaped having an included angle of 135°. However this blade was generally C shaped in cross section having an overhanging roof portion which obscured direct vision of the larynx. Siker proposed using his blade with a mirror but it was found that his laryngoscope was generally not practicable.

It is therefore an object of the invention to provide a laryngoscope which alleviates the problems associated above and which permits visualisation of the larynx and associated structures even in a patient with gross anatomical abnormality.

The invention in one aspect includes a laryngoscope blade having optionally attached thereto a prism and also optionally incorporating a handle integral with or releasably attached to the laryngoscope blade.

The laryngoscope blade of the invention includes two substantially straight portions which are angled with respect to each other so as to form a generally V shaped blade of relatively shallow included angle. Suitably the included angle of the V may be between 120° and 150° and is more appropriately 135°.

The straight portion of the blade proximal or adjacent to the handle may suitably form an included angle with respect to the handle of around 90° to 110° and more preferably 105° to 110°.

Preferably the blade is substantially L shaped in cross section and more preferably is Z shaped with the upright or diagonal of the Z being substantially vertical.

Thus from the foregoing it will be appreciated that the above designated cross section of the blade dispenses with the overhanging roof portion which was included in the generally C shaped cross section of the Siker blade referred to above.

The prism suitable for use with the above described laryngoscope blade may include a prism formed from transparent material which is elongate and is suitably adapted so as to allow insertion of the endotracheal tube which may bear against or be located adjacent to an associated part or surface of the prism.

Preferably the prism may include a leading end surface which may be substantially rectangular and which may slope rearwardly at an acute angle to horizontal and thereafter merge into a top surface which also slopes rearwardly but at a much shallower angle to horizontal before forming a trailing surface which slopes downwardly so that the prism preferably has a base or bottom surface which is substantially oriented in a horizontal plane. There also are suitably provided opposed side surfaces which are substantially planar.

If desired the prism may have a chamfered portion located at the junction of the leading end surface, the top surface and an adjacent side surface.

Reference may now be made to a preferred embodiment of the invention as shown in the attached drawings wherein:

FIG. 1 is a top plan view of a prism suitable for use in the present invention;

FIG. 2 is a side view of the prism shown in FIG. 1;

FIG. 3 is a perspective view of the prism of FIG. 1 and FIG. 2 in combination with a support clip for attachment to a laryngoscope blade;

FIG. 4 is a schematic side view of a laryngoscope blade constructed in accordance with the invention;

FIG. 5 shows an array of cross sectional profiles taken at lines A, B, C, D and E of FIG. 4;

FIG. 6 is a schematic view of the prism of FIG. 1 showing the refraction of light rays passing therethrough;

FIG. 7 is a perspective view of the angulated laryngoscope blade constructed in accordance with the invention;

FIG. 11 is a tip plan view of a modified prism suitable for use with the present invention;

FIG. 12 is a side view of the prism shown in FIG. 11;

FIG. 13 is a side view of another modified prism for use in the present invention;

FIG. 14 is a perspective view of the prism of FIG. 11 in combination with a support clip for attachment to a laryngoscope blade.

FIG. 15 is a perspective view of a curved laryngoscope blade which may be used with the prism of FIG. 1, FIG. 11 or FIG. 13 so as to form a laryngoscope falling with the scope of the invention;

FIG. 16 is an end view of the prism shown in FIG. 13; and

Figure 8:
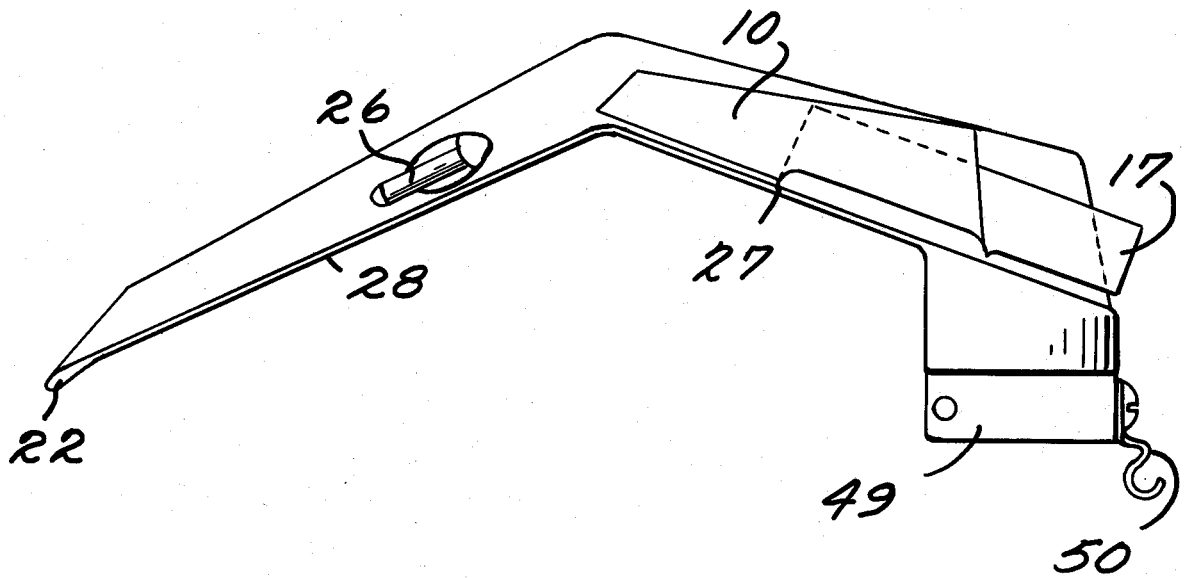
FIG. 8 is a side view of the angulated blade shown in FIG. 7 with a non-chamfered prism attached to the blade.

In the drawings in FIGS. 1-3 the prism 10 includes leading end surface 11, trailing end surface 12, top surface 13, opposed side surfaces 14 and 15 and chamfered portion 16.

The prism 10 may be attached to a laryngoscope blade in any suitable manner which is preferably releasable. Thus in one form prism 10 may be attached to the blade by a spring clip 17 which engages with the blade by virtue of having re-entrant or U shaped part 18 engaging with the vertical web of the blade. Clip 17 also has support surface 19 for engaging with the base surface of the prism 10 as shown in FIG. 3. The clip 17 also includes attachment apertures 20.

The laryngoscope blade 21 shown in FIGS. 4,5,7, and 8 includes tip 22, vertical web 23 forming components 23A and 23B, base flange 24 forming components 24A and 24B and guard 25 as well as lamp 26. As shown in blade forms two straight portions 27 and 28. The progressive cross sectional profile of blade 21 along lines A–E is shown in FIG. 5.

In FIG. 6 there is shown prism 10 having a ray of light 29 from an object 30 which is incident at an angle of 50° 30' to the leading end surface 11 of prism 10. There is also shown another object 30A which directs a ray of light 29A which is incident at an angle of 72° 30' to surface 11 of prism 10. The light rays 29 and 29A are refracted as refracted rays 31 and 32 which reach eye positions 33 and 34 respectively.

Thus FIG. 6 essentially shown the optical diagram of prism 10 and shows how the larynx located at positons 30 and 30A may be viewed at eye positions 33 and 34 respectively. In FIG. 6 there is also shown the respective planes 35 and 36 of surfaces 11 and 12.

Figure 9:
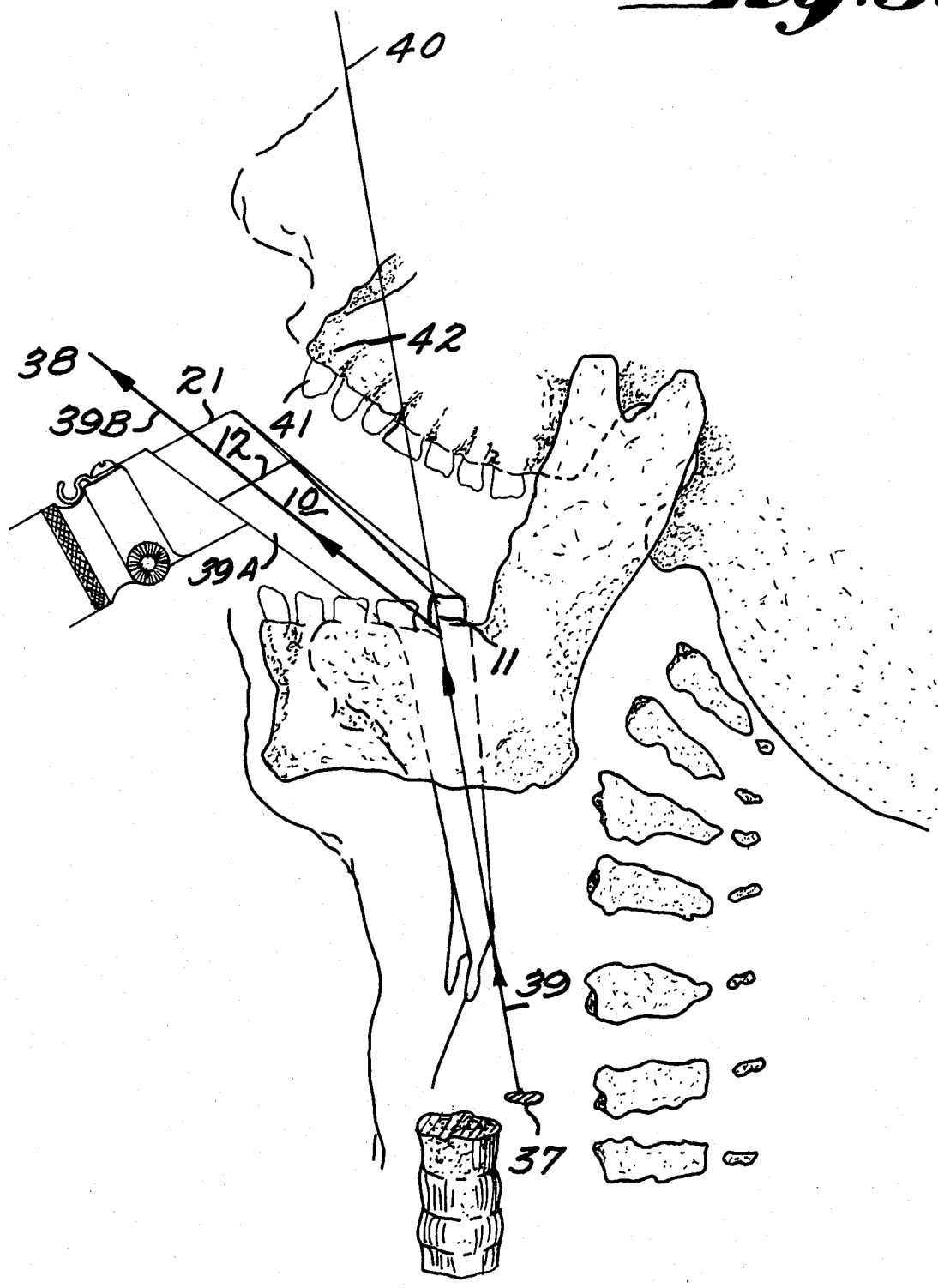
FIG. 9 is a view of the laryngoscope of the invention in use and illustrating how it facilitates visualisation of the larynx.

In FIG. 9 there is shown the prism 10 mounted on laryngoscope blade 21. The corniculate cartilage 37 adjacent to the larynx can be visualised at eye position 38 by ray of light 39 which is refracted through the leading face 11 as refracted ray 39A which is then refracted through the trailing face 12 of prism 10 as refracted ray 39B. The path of the refracted ray of light as described above can then be contrasted with the original path 40 of the light ray travelling from corniculate cartilage 37. The laryngoscope blade 21 is inserted into the mouth and rests against the upper teeth 41. The portion 42 of the maxilla frequently obstructs light path 40 obscuring the view of the larynx. On these occasions a prism may be used as shown in FIG. 9 to refract the light ray 39 from the larynx along the paths 39A and 39B to eye position 38.

The laryngoscope blades of the invention are much narrower and of reduced height when compared to the Macintosh blade being under 16 mm (preferably under 13 mm) in total width and having a maximum height of 21 mm (more preferably under 17 mm) at their highest point. The prism 10 is also narrower to allow room for an endotracheal tube to be inserted into the mouth. The low profile of the distal or leading end 11 of the prism 10 precludes the possiblity of a panoramic view of the glottis but permits visualisation of sufficient structures to allow orientation and intubation even in patients with gross abnormality.

Also the angulated blades of the invention although more easily inserted into the mouth than a straight blade are not quite as easily advanced over the tongue as a continusously curved blade shown in FIG. 15. However, the tongue does not have to be pulled so far anteriorly as with a curved blade. Also there is no curve obstructing light rays approaching the prism from the glottis and as the prism can be positioned more proximally, the combination of laryngoscope blade and prism does not project so prominently against the upper incisor teeth.

Also the laryngoscope blade of the invention may be inserted into a much smaller mouth opening than the Macintosh blade because of its decreased width and more narrow shape. Also the narrow width of the blades of the invention allow them to be pulled more deeply between tongue and tonsil.

Also the laryngoscope blade of the invention is not intrusive and allows room for an endotracheal tube to be inserted past it into the larynx even in patients with gross abnormality.

Figure 10:
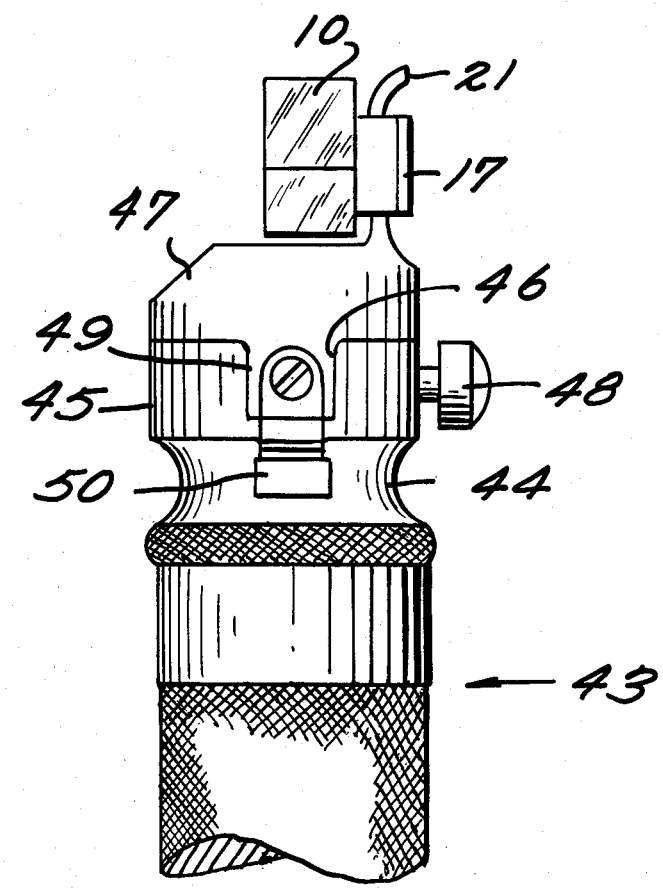
FIG. 10 is a detailed view of the handle of the laryngoscope shown in FIG. 7.

In FIG. 10 there is shown handle 43 having neck portion 44, head portion 45 with notch 46, and bolt 48. The lower part 47 of blade 21 has lower depending portion 49 which locates in notch 46. There is also shown clip 50.

In fact it will be appreciated that the handle of the laryngoscope blade of the invention may be integral with the blade but more preferably is releasably attached thereto such as described above in relation to FIG. 10. Any other type of release attachment can be utilized such as a clip-on or hook-on attachment.

FIGS. 11 and 12 illustrate a modified type of prism 10A and FIGS 13 and 16 illustrate another type of prism 10B suitable for use in the invention which each omit chamfered part 16 of the prism shown in FIGS. 1-3. This chamfered part is useful however in that it provides more access for the endotracheal tube when inserted through the mouth. FIG. 14 illustrates prism 10A being attachable to support clip 17.

Figure 17:
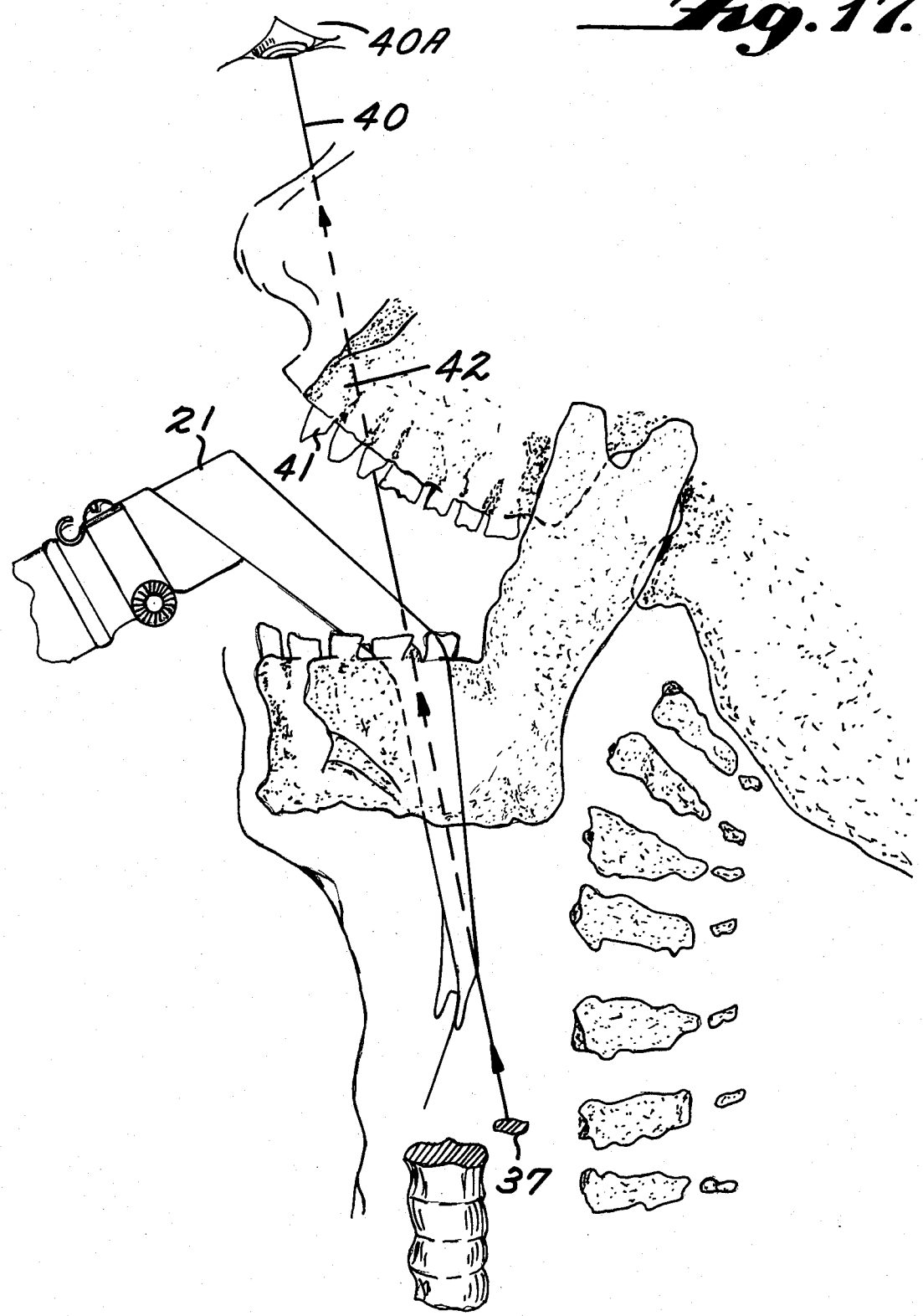
FIG. 17 is a view of the laryngoscope of the invention in use and illustrating how it facilitates visualisation of the larynx in some patients without the need to attach a prism.

FIG. 17 shows that the corniculate cartilage 37 as being directly visible by use of the laryngoscope blade 21 of the invention by light ray 40 reaching eye position 40A. In fact the blade 21 in most cases can be used without prism 10 to allow a direct view of the larynx in contrast to the prior art previously discussed. As in the case of FIG. 9, there is also shown a tip 22 of blade 21 lying behind or in a location posterior to epiglottis 51 and pressiong against same so as to facilitate a direct view of larynx or trachea 52 to be obtained along straight portion 28.

The angulated laryngoscope blade of the invention suitably has an overall length measured in a straight line of 90–210 mm for adults and 70–85 mm (preferably 77 mm) for infants. Component 24A of the base flange 24 has a length suitably of 40–120 mm (preferably 60–85 mm) with a length of 50 mm being suitable for infants while component 24B suitably has a length of 50–90 mm (preferably 60–75 mm) with a length of 22–32 mm (preferably 27 mm) being suitable for infants. On the other hand, the width of flange 24 is suitably within the range of 7–16 mm (preferably 11–13 mm) and the height of web 23A is suitably within the range of 6–14 mm at its junction with component 23B to 11–21 mm at its end adjacent handle 43. Component 23B may have a height of 2–8 mm adjacent the tip 22 which thereafter may gradually increase to the limits already described above in relation to web 23A at its junction with component 23B.

In relation to the prisms shown in FIGS. 2,12 and 16 it will be noted that various lengths $l_1$, $l_2$, $l_3$, $l_4$, $l_5$ and $l_6$ are depicted thereon with angles X, X1, X2, X3, X4 and X5.

It is preferred that $l_1$ has a length of 27–63 mm (preferably 43–48 mm) $l_2$ has a length of 12–22 mm (preferably 14–18 mm), $l_3$ has a length of 30–70 mm (preferably 40–55 mm) and $l_4$ has a length of 4–11 mm (preferably 6–8 mm).

In regard to FIG. 16 which shows a modified prism having a modified trailing face with components 12A and 12B, $l_5$ may have a length of 7–13 mm (preferably 9–10 mm) and $l_6$ have a length of 5–9 mm (preferably 6–7.5 mm).

In relation to the angles, angle X may have a value of 50°–75° (preferably 60°–65°) X1 may have a value of 115°–135° (preferably 122°–130°) X2 may have a value of 85°–105° (preferably 92°–102°) X3 may have a value of 65°–90° (preferably 70°–80°) X4 may have a value of 165°–175° (preferably 168°–173°) and X5 may have a value of 78°–90° (preferably 83°–87°).

The widths of the prism may vary from 5–15 mm (more preferably 8–10 mm). The prism may be made from any suitable transparent material such as glass or plastics material (e.g. cast allyl diglycol carbonate monomer known as "CR-39", methylmethacrylate polymer (known as "Perspex" "Plexiglas" or "Origlas") and polycarbonate material).

The refractive index of the transparent material may range from 1.40 to 1.65 and is preferably from 1.47 to 1.55.

The prism of the invention does have advantages over the prior art such as the Huffman prism in that the angles of the leading and trailing faces as described above provide greater bending of light rays from the larynx as shown in FIGS. 6 and 9 and less deviation of the emergent ray from the prism as the ray of light leaves the prism as also shown in FIGS. 6 and 9. And is about ⅓ the volume of the Huffman prism.

Moreover, in contrast with the Huffman prism, it has the outstanding advantage of actually being usable and useful in clinical practice for those patients who are otherwise difficult or impossible to intubate.

The prism of the invention when compared to the Huffman prism has a selectively short base for greater bending of light which is particularly useful with the angulated laryngoscope blade of the invention. It is also of narrower dimensions to allow greater access for the endotracheal tube and also for the blade. It also has a reduced height when compared to the Huffman prism so that it is less intrusive against the teeth.

Therefore in another aspect of the invention there is provided a prism as described above which does not necessarily have to be used with the angulated blade of the invention and which can also be used with a conventional blade but more preferably a curved blade as shown in FIG. 15.

I claim:
1. A laryngoscope comprising a handle and a blade, said handle having a first end and said blade having a first end attached to said first end of said handle, said blade including a pair of opposed, substantially straight component means disposed so as to form a generally V-shaped blade, a first one of said pair of component means including said first end of said blade, the second one of said pair having an end including a tip remote from said first component means and extending from the end of said second one of said component means, said pair of component means forming between them an included angle of approximately 135 degrees, the ratio of the length of one of said component means to length of the other component means being within the range of 4:5 to 4:3 so that full insertion of said tip and said second one of said component means followed by said first one of said component means into the mouth and throat of a patent will be permitted not only for the normal patient but also for a substantial number of patients having abnormalities where the user is not able to hold the tongue forward from the line of vision to allow a view of the larynx but which view is obtainable by pressing said tip posterior to the epiglottis to allow the epiglottis to be moved formwardly to facilitate a view of the larynx along said second one of said pair of component means, either by direct vision or by indirect vision through an appropriately fitted prism.

2. A laryngoscope blade as claimed in claim 1 wherein the blade is substantially Z shaped in cross section througout at least part of its length with the upright or diagonal of the Z being substantially vertical and the top arm of the Z being reduced in length relative to the bottom arm.

3. The laryngoscope as claimed in claim 1 wherein said second one of said component means is substantially planar adjacent said tip.

4. A laryngoscope blade as claimed in claim 3 having an overall length measured in a straight line of 90–210 mm for adults and 70–85 mm for infants.

5. A laryngoscope blade as claimed in claim 4 wherein the height of the vertical web or component of the L or Z is between 2–21 mm and the width of the horizontal component or arm of the L or Z is between 7–16 mm.

6. The laryngoscope blade as claimed in claim 3 wherein said first component means includes a straight portion of the blade located adjacent said handle, said straight portion being substantially L-shaped with both arms of the L being substantially equal in length.

* * * * *